(12) United States Patent
Schroeder

(10) Patent No.: US 9,827,375 B2
(45) Date of Patent: Nov. 28, 2017

(54) HIGH PRESSURE DELIVERY SYSTEM AND METHOD FOR TREATING PELVIC DISORDER USING LARGE MOLECULE THERAPEUTICS

(71) Applicant: AMS Research Corporation, Minnetonka, MN (US)

(72) Inventor: Tania M. Schroeder, Minnetonka, MN (US)

(73) Assignee: Astora Women's Health Holdings, LLC, Minnetonka, MN (US)

( * ) Notice: Subject to any disclaimer, the term of this patent is extended or adjusted under 35 U.S.C. 154(b) by 0 days.

(21) Appl. No.: 14/659,095

(22) Filed: Mar. 16, 2015

(65) Prior Publication Data

US 2015/0182701 A1 Jul. 2, 2015

Related U.S. Application Data

(62) Division of application No. 13/328,674, filed on Dec. 16, 2011, now Pat. No. 8,979,797.

(Continued)

(51) Int. Cl.
*A61K 38/00* (2006.01)
*A61M 5/30* (2006.01)
(Continued)

(52) U.S. Cl.
CPC ....... *A61M 5/3015* (2013.01); *A61K 31/7105* (2013.01); *A61K 38/00* (2013.01); *A61M 25/0084* (2013.01); *A61M 2025/0079* (2013.01)

(58) Field of Classification Search
CPC ................. A61B 17/1114; A61B 17/42; A61F 2250/0067; A61K 38/00; A61M 2025/0079; A61M 25/0084
(Continued)

(56) References Cited

U.S. PATENT DOCUMENTS 4,093,108 A 6/1978 Hein et al.
4,130,119 A 12/1978 Sessions et al.
(Continued)

FOREIGN PATENT DOCUMENTS

WO 96166066 A1 6/1996
WO 9736625 A1 10/1997
(Continued)

OTHER PUBLICATIONS

Anthony Atala, M.D., Future Perspectives in Reconstructive Surgery Using Tissue Engineering, Urologic Clinics of North America, Reconstructive Urology, vol. 26, No. 1 (Feb. 1999) pp. 157-165.
(Continued)

*Primary Examiner* — Gerald Landry, II
(74) *Attorney, Agent, or Firm* — Kagen Binder, PLLC

(57) ABSTRACT

The invention relates generally to methods and systems for the treatment of pelvic tissues using a high pressure injection device to deliver a therapeutic composition that includes a large molecule therapeutic agent, such as a nucleic acid or a polypeptide, to a target tissue in the pelvic area. Methods of the invention can improve delivery of the therapeutic agent into the tissue, which can be beneficial for the treatment of a pelvic tissue disorder, such as bladder and prostate tumors.

11 Claims, 1 Drawing Sheet

Related U.S. Application Data

(60) Provisional application No. 61/423,651, filed on Dec. 16, 2010.

(51) Int. Cl.
*A61K 31/7105* (2006.01)
*A61M 25/00* (2006.01)

(58) Field of Classification Search
USPC .................................. 514/1.1, 44 R; 604/508
See application file for complete search history.

(56) References Cited

U.S. PATENT DOCUMENTS

| | | | |
|---|---|---|---|
| 4,742,817 A | 5/1988 | Kawashima et al. | |
| 4,946,442 A | 8/1990 | Sanagi | |
| 5,007,897 A | 4/1991 | Kalb et al. | |
| 5,116,313 A | 5/1992 | McGregor | |
| 5,261,889 A | 11/1993 | Laine et al. | |
| 5,336,178 A | 8/1994 | Kaplan et al. | |
| 5,693,016 A | 12/1997 | Gumaste et al. | |
| 5,840,062 A | 11/1998 | Gumaste et al. | |
| 6,203,533 B1 | 3/2001 | Ouchi | |
| 6,210,378 B1 | 4/2001 | Ouchi | |
| 6,238,336 B1 | 5/2001 | Ouchi | |
| 6,280,413 B1 | 8/2001 | Clark et al. | |
| 6,400,980 B1 | 6/2002 | Lemelson | |
| 6,537,205 B1 | 3/2003 | Smith | |
| 6,541,039 B1 | 4/2003 | Lesniak et al. | |
| 6,547,767 B1 | 4/2003 | Moein | |
| 6,641,553 B1 | 11/2003 | Chee et al. | |
| 6,866,842 B1 | 3/2005 | Chancellor et al. | |
| 6,905,475 B2 | 6/2005 | Hauschild et al. | |
| 6,979,466 B2 | 12/2005 | Lesniak et al. | |
| 7,115,417 B1 * | 10/2006 | Chancellor | C12N 5/0659 435/325 |
| 7,553,662 B2 | 6/2009 | El Haj et al. | |
| 7,594,900 B1 | 9/2009 | Nash et al. | |
| 7,625,562 B2 | 12/2009 | El Haj et al. | |
| 7,749,156 B2 | 7/2010 | Ouchi | |
| 8,979,797 B2 | 3/2015 | Schroeder | |
| 2003/0096774 A1 * | 5/2003 | Gonda | A61K 31/704 514/44 A |
| 2003/0161816 A1 | 8/2003 | Fraser et al. | |
| 2003/0163111 A1 | 8/2003 | Daellenbach | |
| 2003/0181917 A1 * | 9/2003 | Gertner | A61M 35/003 606/82 |
| 2004/0013652 A1 | 1/2004 | Marko et al. | |
| 2004/0162528 A1 | 8/2004 | Horvath et al. | |
| 2005/0025755 A1 | 2/2005 | Hedrick et al. | |
| 2005/0163711 A1 * | 7/2005 | Nycz | A61K 9/0021 424/9.1 |
| 2005/0192530 A1 | 9/2005 | Castellano | |
| 2005/0222027 A1 | 10/2005 | Chiang et al. | |
| 2005/0228225 A1 | 10/2005 | Hauschild et al. | |
| 2006/0039896 A1 | 2/2006 | Kleinsek et al. | |
| 2006/0045872 A1 | 3/2006 | Miguel et al. | |
| 2006/0129125 A1 | 6/2006 | Copa et al. | |
| 2006/0142732 A1 * | 6/2006 | Karmarkar | A61M 25/0138 604/508 |
| 2007/0167921 A1 | 7/2007 | Burren et al. | |
| 2007/0225554 A1 | 9/2007 | Maseda et al. | |
| 2007/0231360 A1 * | 10/2007 | Peyman | A61K 9/51 424/422 |
| 2008/0114203 A1 | 5/2008 | Crank | |
| 2008/0119784 A1 | 5/2008 | Roychowdhury et al. | |
| 2008/0119823 A1 | 5/2008 | Crank | |
| 2008/0267927 A1 | 10/2008 | Lutz et al. | |
| 2008/0286361 A1 | 11/2008 | Dobson et al. | |
| 2008/0305152 A1 * | 12/2008 | Kleinig | A61K 8/64 424/443 |
| 2009/0004281 A1 * | 1/2009 | Nghiem | A61K 9/0004 424/490 |
| 2009/0082611 A1 | 3/2009 | Levy et al. | |
| 2009/0123366 A1 | 5/2009 | Dobson et al. | |
| 2009/0124974 A1 | 5/2009 | Crank et al. | |
| 2009/0180965 A1 | 7/2009 | Freyman et al. | |
| 2009/0192083 A1 | 7/2009 | Currie | |
| 2009/0312696 A1 | 12/2009 | Copa et al. | |
| 2010/0105621 A1 * | 4/2010 | Cohen | A61K 38/1875 514/1.1 |
| 2010/0120668 A1 * | 5/2010 | Wolgen | A61K 38/34 514/10.7 |
| 2010/0254939 A1 * | 10/2010 | Kissel | A61K 9/5138 424/85.2 |
| 2010/0298816 A1 | 11/2010 | Dobson | |
| 2011/0008299 A1 * | 1/2011 | Koullick | A61K 35/12 424/93.7 |
| 2011/0015614 A1 | 1/2011 | Rykhus, Jr. et al. | |
| 2011/0034753 A1 | 2/2011 | Dobson et al. | |
| 2011/0046600 A1 | 2/2011 | Crank | |
| 2011/0077456 A1 * | 3/2011 | Drummond | A61F 2/0045 600/30 |
| 2011/0274757 A1 * | 11/2011 | Nelson | A61K 9/1611 424/489 |
| 2011/0282318 A1 | 11/2011 | Crank et al. | |
| 2012/0039992 A1 * | 2/2012 | Hazan | A61K 36/22 424/450 |
| 2012/0184805 A1 * | 7/2012 | Pulliam | A61B 17/0625 600/37 |
| 2013/0338210 A1 * | 12/2013 | Manoharan | C07C 217/08 514/44 A |

FOREIGN PATENT DOCUMENTS

| | | | | |
|---|---|---|---|---|
| WO | | 0040279 A1 | 7/2000 | |
| WO | | 0066199 A1 | 11/2000 | |
| WO | | 0136029 A1 | 5/2001 | |
| WO | | 0207812 A1 | 1/2002 | |
| WO | | 2004000369 A2 | 12/2003 | |
| WO | | 2004071612 A2 | 8/2004 | |
| WO | | 2005094921 A1 | 10/2005 | |
| WO | | 2006057604 A1 | 6/2006 | |
| WO | | 2006063180 A2 | 6/2006 | |
| WO | | 2006076699 A1 | 7/2006 | |
| WO | | 2006084821 A2 | 8/2006 | |
| WO | | 2006086719 A2 | 8/2006 | |
| WO | | 2007038591 A2 | 4/2007 | |
| WO | | 2007079152 A2 | 7/2007 | |
| WO | | 2010065126 A2 | 6/2010 | |
| WO | | 2010065127 A2 | 6/2010 | |
| WO | | 2010065133 A2 | 6/2010 | |
| WO | WO | 2010065133 A2 * | 6/2010 | ............ A61M 25/00 |
| WO | | 2010074705 A2 | 7/2010 | |
| WO | | 2010077271 A2 | 7/2010 | |
| WO | | 2011011423 A1 | 1/2011 | |

OTHER PUBLICATIONS

Alfred E. Bent et al., Treatment of Intrinsic Sphincter Deficiency Using Autologous Ear Chrondrocytes as a Bulking Agent, Neurology and Urodynamics 20: 157-165 (2001).

Stanislav Berjukow, et al., Membrane Properties of Single Muscle Cells of the Rhabdosphincter of the Male Urethra, The Prostate 58:238-274 (2004).

Teruhiko Yokoyama et al., Persistence and Survival of Autologous Muscle Derived Cells Versus Bovine Collagen as Potential Treatment of Stress Urinary Incontinence, The Journal of Urology, vol. 165; 171-276, Jan. 2001.

* cited by examiner

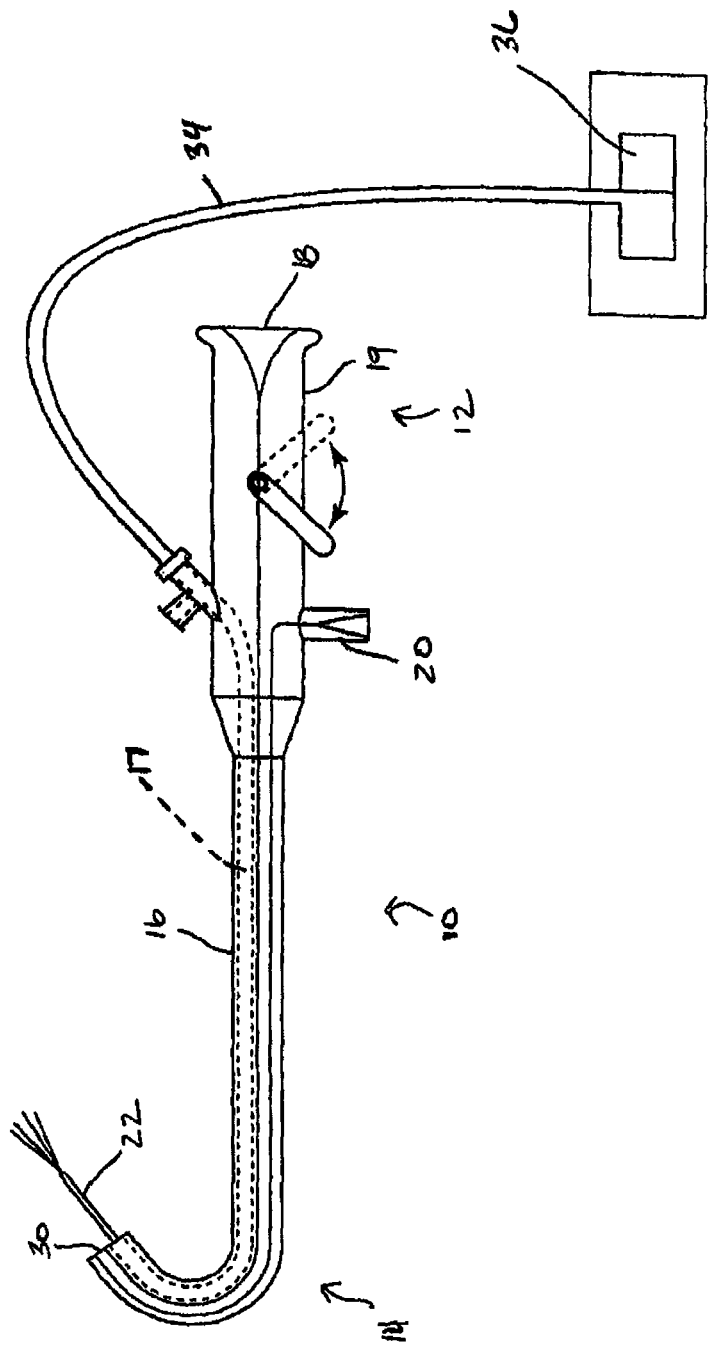

HIGH PRESSURE DELIVERY SYSTEM AND METHOD FOR TREATING PELVIC DISORDER USING LARGE MOLECULE THERAPEUTICS

PRIORITY

This application is a divisional of application Ser. No. 13/328,674, filed Dec. 16, 2011, which claims the benefit of U.S. Provisional Patent Application Ser. No. 61/423,651, filed Dec. 16, 2010, entitled GENE THERAPY DELIVERY SYSTEM AND METHOD OF GENE TREATMENT, the disclosures of which are incorporated herein by reference.

FIELD OF THE INVENTION

The invention relates generally to surgical tools and methods and, more particularly, to methods and devices for treating tissue in the pelvic area using needleless or high-pressure jet injection devices for injecting fluid into tissue.

BACKGROUND OF THE INVENTION

Pelvic health is an increasingly important health issue, e.g., based on an aging population. Treatment of pelvic conditions, such as urinary continence is an area of much investigation. Such conditions are desired to be treated with therapeutic agents as opposed to invasive surgical procedures, when possible, in order to avoid risks of surgical procedures, such as infection, and recovery period and pain for the patient. Therapeutic agents should be delivered with minimized discomfort and procedure time, and with the best degree of accuracy of delivery location and delivery volume as possible. As such, there exists continuing need to provide improved treatment methods and devices for delivering therapeutic fluids to the pelvic region of a patient.

One type of disease of the pelvic tissue is bladder cancer, which is the second most common urological malignancy. Most bladder tumors are not invasive into the bladder muscle layer (also known as superficial tumors). Non-invasive bladder cancer is commonly treated using surgical transurethral resection of the bladder tumor to take out the lesion. Recurrence of non-invasive bladder cancer is about 50% and depends on certain prognostic factors such as tumor grade, tumor stage, and in situ carcinoma. Intravesical chemotherapy following surgical resection of the bladder tumor is often carrier out to delay or prevent recurrence or progression to muscle-invasive bladder cancer. Despite surgical resection and intravesical therapy, in a considerable percent of patients superficial lesions will recur, with some recurring lesions progressing to a higher grade or stage that form invasive cancers. Local invasive cancer of the bladder is typically treated by radical cystectomy, but this can result in the loss of pelvic floor functions and adversely affect the patient quality of life.

Prostate disease is another pelvic floor disease that poses significant health risks for males. Diseases of the prostate include prostatitis, benign prostatic hyperplasia (BPH, also known as benign prostatic hypertrophy), prostatic intraepithelial neoplasia (PIN), and prostatic carcinoma.

SUMMARY OF THE INVENTION

The invention relates generally to systems and methods for treating a patient having a pelvic floor disease using a high-pressure injection device to deliver a therapeutic composition that includes a large molecule therapeutic agent useful for treating the disease.

In one aspect, the invention provides a method for treating or preventing a disease of the pelvic floor. The method comprises a step of delivering a composition to a tissue selected from bladder, prostrate, urethral, kidney, vaginal, and rectal tissues, where the composition is delivered to the tissue using a pressure in the range of 100 psi to 4000 psi. The composition includes a therapeutic agent selected from the group consisting of nucleic acids and polypeptides and the therapeutic agent treats or prevents the disease in the tissue.

In another aspect, the invention provides a system for treating or preventing a disease of the pelvic floor. The system comprises a high-pressure delivery device that comprises a pressure source and a fluid compartment that can house a therapeutic composition. The device is capable of delivering the composition to the tissue with a pressure in the range of 100 psi to 4000 psi. The composition includes a therapeutic agent selected from the group consisting of nucleic acids and polypeptides. In the system, the composition can be pre-leaded in the device, or can be added to a fluid compartment of the device prior to delivering the composition.

In some modes of practice, the method and system can provide gene therapy which delivers DNA to cells to treat diseases based on genetic mutation, to alter the expression of particular proteins, or to cause apoptosis. Specific genes can be transcribed and then translated into proteins, or the nucleic acid can prevent gene expression by antisense or an interference RNA pathway. In one application, naked DNA is delivered into tissues of the pelvic floor to treat or prevent pelvic flood condition. In another application, nucleic acid is included in a viral particle, a nanoparticle, or both, and delivered into tissues of the pelvic floor to treat or prevent pelvic flood condition. Genes and proteins could be delivered for other purposes, such as increasing or enhancing angiogenesis, wound healing, smooth muscle relaxation, or to correct a genetic mutation. One delivery means includes jet injection, which offers increased gene expression relative to needle injection.

BRIEF DESCRIPTION OF THE DRAWINGS

FIG. 1 illustrates an injection catheter system in accordance with embodiments of the present invention.

DETAILED DESCRIPTION

The invention relates to treatment methods and devices useful for delivering (e.g., injecting or instilling) a large molecule therapeutic agent to tissue at or near target pelvic structures, such as the pelvic floor. Large molecule therapeutic agents are represented by those such as polypeptides, including proteins, and nucleic acids, such as RNA and DNA, and can include specific genes that can be transcribed and then translated into proteins.

In one example, naked DNA is delivered into tissues of the pelvic floor to address one of a variety of pelvic health issues. Genes (and therefore proteins) could be delivered for many other purposes, including but not limited to, increasing or enhancing angiogenesis, wound healing, and smooth muscle relaxation, to correct a genetic mutation or to cause apoptosis. One delivery means includes jet injection, which advantageously offers increased gene expression relative to needle injection. However, needle injection, including micro needles, is included within the scope of the invention.

The invention relates generally to surgical tools and methods and, more particularly, to methods and devices for treating tissue of the urinary tract (e.g., prostate tissue, kidneys, ureters, urethral tissue, bladder, etc.) of a subject, using needleless or high-pressure jet injection devices for injecting fluid into tissue. The terms "patient" and "subject" are used herein to refer to mammals that can receive treatment using the high-pressure injection device and associated methods. The mammal treated can be a human subject or a non-human subject, such as domesticated pets, farm animals, and experimental animals, including, but not limited to dogs, cats, rabbits, rats, mice, sheep, horses, and cows.

Administration of the compositions using the high pressure injection device can prevent or delay the onset of the symptoms of a disease (or condition or disorder) of the pelvic tissue, can be used to alleviate or ameliorate symptoms, or halt further progression of the disease. Success in treating disease (or condition or disorder) of the pelvic tissue can be assessed by objective or subjective parameters, including imaging of the treatment site, biochemical or histological analysis of blood or tissue, and examination by a physician.

In some modes of practice the high-pressure jet injection device injects a fluid composition that includes a nucleic acid which becomes incorporated into cells of the particular pelvic tissue that was targeted. The nucleic acid is incorporated into, or "taken up" by the cells, and, in some cases, the cells biochemical machinery express the incorporated nucleic acid. Cells that have incorporated the nucleic acid can be referred to herein as "transformed" or "transgenic" by the virtue of the nucleic acid having been incorporated into the cells.

A "nucleic acid," as used herein can be any polynucleotide molecule of covalently-bonded nucleotide monomers, i.e., a deoxyribonucleotide or ribonucleotide polymer in either single- or double-stranded form, which can include analogs of natural nucleotides. The nucleic acid can include those that are natural, synthetically-prepared, modified (e.g., a nucleic acid derivative), and enzymatically-treated. Exemplary nucleic acids include, but are not limited to, DNA and RNA, modified DNA and RNA, antisense oligonucleotides, antisense iRNA (immune ribonucleic acid), ribozymes, siRNA (small/short interfering RNA), and shRNA (small/short hairpin RNA). The nucleic acid can be a part of a plasmid, a phage, a cosmid, and episome, or an integratable DNA fragment. The nucleic acid used to treat the pelvic floor condition can be isolated from a variety of sources, genetically engineered, amplified, and/or expressed/generated recombinantly, or chemically synthesized in vitro.

Antisense RNA and DNA are single-stranded polynucleotides (e.g, deoxyribonucleotide or ribonucleotide polymers) which can be complimentary to a messenger RNA (mRNA) strand. Antisense polynucleotides can be introduced into a cell and base pair to mRNA thereby physically obstructing the translation complex and inhibiting translation. One or more particular genes can be targeted for antisense inhibition which results in decreased expression of the gene(s) which can be beneficial for the treatment of a disease associated with pelvic tissue. The antisense oligonucleotide can be complementary to and capable of hybridizing to a target nucleic acid. The antisense oligonucleotide can have a length of less than 100 bases, such as about 10 to about 50, or about 15 to about 40, bases in length.

The methods of the invention can be used to affect a process of RNA interference in cells of the target tissue, which involves RNA-dependent gene silencing. An RNA molecule, such as short double-stranded RNA, is introduced into the cytoplasm, where it interacts with proteins to form an RNA-induced silencing complex (RISC). After integration into the RISC, the interfering RNA base-pairs to its target mRNA and induces cleavage, which prevents the mRNA from being used as a translation template. siRNA is short (generally about 20-25 nucleotides in length) double-stranded RNA which can be used to interfere with expression of a specific gene via the RNA interference (RNAi) pathway. shRNA includes a RNA sequence and has a structure that includes hairpin turn that can silence gene expression also via the RNA interference (RNAi) pathway. A shRNA approach may include use of stRNA (small temporal RNA) (Paddison (2002) Genes Dev. 16, 948-958).

In some arrangements, the nucleic acid can be present on a vector or expression cassette from which the gene can be expressed after it is introduced into the cell. The vector or expression cassette can include a promoter operably linked with the gene sequence that is desired to be expressed. The promoter can be a tissue specific promoter for expression in a target pelvic tissue, such as the promoters for the uroplakins genes UP1a and UP2 which can provide bladder tissue-specific expression. Optionally the vector or expression cassette can include other sequences, such as transcription termination signals or enhancers helpful in effecting expression. A nucleic acid can be considered to be operably linked to another nucleic acid when the sequences are placed into a functional relationship with each other, such as a promoter operably linked to a coding sequence which affects the transcription of the sequence. The vector can be capable of transporting the desired nucleic acid and any other sequence to which it can be operably linked. Plasmid vectors are generally circular double stranded DNA loops into which DNA segments can be ligated. In viral vectors DNA segments can be ligated into the viral genome. Some vectors (e.g., non-episomal mammalian vectors) can be integrated into the genome of a host cell upon introduction into the host cell, and thereby are replicated along with the host genome.

Exemplary vectors include viral vectors, plasmids, phages, phagemids, cosmids, and bacteriophages. Exemplary viral vectors include adenovirus vectors, retroviral vectors, and adeno-associated viral vectors. In some cases the cloning vehicle can comprise a plasmid or a bacteriophage P1-derived vector (PAC).

A nucleic acid can be administered to a target pelvic tissue using the high pressure injection device as "naked DNA" (see, e.g., U.S. Pat. No. 5,580,859) or in the form of an expression vector, e.g., a recombinant virus. Vectors administered in vivo can be derived from viral genomes, including recombinantly-modified enveloped or non-enveloped DNA and RNA viruses, such as from baculoviridiae, parvoviridiae, picornoviridiae, herpesviridiae, poxviridae, adenoviridiae, or picornaviridiae. Chimeric vectors can also be employed which exploit advantageous merits of each of the parent vector properties (See e.g., Feng, Nature Biotechnology 15:866-870, 1997). Such viral genomes can be modified by recombinant DNA techniques to include the nucleic acids for treating a pelvic floor disease, including those described herein; and can be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096, 718; 6,110,458; 6,113,913; 5,631,236), adeno-associated viral, or retroviral genomes. Retroviral vectors can include those based upon murine leukemia virus (MuLV), gibbon ape leukemia virus (GaLV), Simian Immuno deficiency virus (SIV), or human immuno deficiency virus (HIV); see, e.g., U.S. Pat. Nos. 6,117,681; 6,107,478; 5,658,775; 5,449,614; Buchscher, J. Virol. 66:2731-2739, 1992; Johann, J. Virol. 66:1635-1640, 1992).

In some aspects of the invention, the therapeutic composition includes a polypeptide. A polypeptide refers to an oligomer or polymer of two or more amino acid residues linked by amide (peptide) bond(s). Polypeptides encompass compounds referred to in the art as proteins, oligopeptides, peptides, and the like. Peptides are short polypeptides and typically characterized by containing less than 50 monomer units. Proteins are made from one or more polypeptides and are typically folded to facilitate a biological function. Specific classes of polypeptides include, but are not limited to, enzymatic polypeptides (enzymes), antibodies, antibody fragments, neuropeptides, and peptide hormones. Polypeptides can include common, naturally-occurring amino acids residues, including rare naturally-occurring amino acids, non-natural amino acids, or combinations thereof. Incorporation of non-natural amino acids into a polypeptide may serve to increase the stability, reactivity and/or solubility of the polypeptide. Polypeptides can also include those that are modified with, or conjugated to, a biomolecule that is not a polypeptide. For example, the polypeptide can be a polysaccharide-peptide conjugates (e.g., glyosylated polypeptides; glycoproteins), a poly(ethyleneglycol)-polypeptide conjugate (PEG-ylated polypeptides), or a peptide-nucleic acid (PNA) conjugate.

The system and methods of the invention using the high pressure injection devices can be used to treat various types of bladder diseases including bladder cancer. Urothelial carcinoma (transitional cell carcinoma) is the most common type of bladder cancer (greater than 90%) in which the normal cells forming the innermost lining of the bladder wall undergo uncontrolled cell growth. Squamous cell carcinomas, representing 3%-8% of the bladder cancers, typically result from chronic bladder irritation or inflammation and originate from the thin, flat cells. Adenocarcinomas of the bladder are the least common (1%-2%). Transitional cells normally line the rest of the urinary tract including the kidneys, the ureters, the bladder, and the urethral and urothelial carcinoma can develop in any of these areas.

Bladder cancers can be classified based on the extent of invasion, either superficial or invasive, into the bladder wall, which has several layers. In superficial bladder cancer, characteristic of urothelial cell carcinomas, the mucosa and lamina propria are only affected, which are the innermost linings of the bladder. In invasive bladder cancers, characteristic of adenocarcinomas and squamous cell carcinomas, the cancerous growth has at least penetrated the muscular layer of the bladder wall. Bladder cancers are also typically characterized as low grade which are less aggressive growths, or high grade which are more aggressive growths and display abnormal, phenotypically changed cells. Urothelial carcinomas can be in the form of papillary tumors which grow as finger-like projections into the lumen of the bladder. Cancerous growth in the bladder can also develop in the form of a flat, red (erythematous) patch on the mucosal surface, referred to as carcinoma-in-situ (CIS).

In some modes of practice a nucleic acid-containing composition includes one or more nucleic acid types which are used to treat tumor or cancerous tissue, and is delivered to the area of diseased tissue using high pressure injection. Many approaches for treating tumor or cancerous tissue involve using the administered nucleic acid to cause suppression of the function of activated oncogenes, to initiate tumor self-destruction, or to restore the expression of functional tumor suppressor genes. Exemplary targets of gene therapy for the treatment of bladder cancer include the p53 tumor suppressor, transcription factors ZEB1 and ZEB2 involved in the epithelial-mesenchymal transition (EMT), epidermal growth factor receptor (EGFR)-related pathways, and genes involved in anti-angiogenic pathways.

Viral vectors can be used to deliver a desired nucleic acid. Viral vectors such as the adeno-associated virus (AAV) vector have been reported to be non-pathogenic and offer long-term transgene expression in vivo, and can include a desired nucleic acid for therapy of the target pelvic tissue. For example, the suppression effect of AAV-mediated HSV-TK/GCV system on bladder cancer cells and in mice xenograft models of bladder cancer has been investigated, and suggests that a rAAV-HSV-TK system can control tumour cell growth and provide strong anti-tumour efficacy in vivo. (Pan, J. G., et al. (2011) Med Oncol. 2011).

In some modes of practice, the methods of the invention use of the nucleic acid composition to initiate tumour self-destruction through an apoptotic cell pathway (i.e., "suicide gene therapy") for treating diseases of the pelvic system that are associated with unregulated cellular growth. An exemplary therapeutic nucleic acid encodes encodes herpes simplex virus thymidine kinase (HSV-TK), which, when expressed in a target cell can phosphorylate ganciclovir (GCV) and be used to kill the cells. Phosphorylated GCV can interact with cellular DNA polymerase and interfere with the synthesis of DNA resulting in the death of dividing cells of the tumor tissue (Pan, J. G., et al. (2011) Med Oncol. 2011). To further illustrate this type of nucleic acid technology, bifidobacterium infantis-mediated thymidine kinase (BI-TK) gene therapy was used in a rat model of bladder tumors by transformation of pGEX-TK (Tang W, et al. (2009) J Exp Clin Cancer Res. 28:155). After pGEX-TK was administered, ganciclovir (GCV) was intraperitoneally injected. Apoptosis was mostly notable in the BI-TK/GCV treatment group which had the highest level of caspase3 protein expression, resulting in inhibition of rat bladder tumor growth.

Another exemplary therapeutic nucleic acid encodes the Tumor necrosis factor (TNF)-related apoptosis inducing ligand (TRAIL), which is a member of the TNF superfamily of cytokines and induces apoptosis in a variety of cancer cells, with minimal toxicity to normal cells. To illustrate this type of nucleic acid technology, introduction of the human TRAIL gene into TRAIL-sensitive tumor cells using an adenoviral vector has been shown to result in the rapid production and expression of TRAIL protein, followed by the death of the tumor cells (J. Immunol. (2000) 165:2886-94). Apoptosis was evidenced by certain cellular events including the activation of caspase-8 and the binding of annexin.

In some modes of practice, the methods of the invention target inhibitors of apoptosis, such as members of the inhibitor of apoptosis protein (IAP) family, with a nucleic acid for the treatment of bladder tumors. (IAPs) are highly conserved, are characterized by 70 amino acid baculoviral repeats (BIR), and have wide spread roles in anti-apoptotic functions. Livin is an IAP family member that can inhibit apoptosis by inhibiting an inhibitor of IAPs. Livin expression has been reported in various tumor cells and its overexpression of this gene appears to be cancer cell specific. To illustrate this type of technology, in one study phosphorathioate modifying was used to synthesize antisense oligonucleotides targeting Livin, followed by transfection into human bladder cancer cell 5637 (Liu, C., et al. (2010) J Exp Clin Cancer Res. 29:63). Livin antisense nucleotide effectively inhibited Livin expression and tumor cell proliferation through enhanced caspase3 activity and apoptosis of tumor cells. In a nude mouse transplantable tumor model, Livin expression was inhibited and caspase3 expression was increased resulting in enhanced apoptosis and slowed tumor growth.

Survivin is an anti-apoptotic protein expressed in many cancerous growths. Survivin inhibits apoptotic enzymes, and its overexpression leads to uncontrolled cancer cell growth. Downregulation of survivin expression has been targeted as a way to sensitize tumor cells to promote cell apoptosis. To illustrate this type of technology, in one study small interfering RNA (siRNA) targeting survivin was transfected into T24 cells using a liposome approach, which resulted in a decrease in survivin protein (Ku, J. H., et al. (2010) BJU Int. 106:1812-6). This correlated with a decrease in cell growth, G2/M arrest, and an increase in the fraction of cells undergoing apoptosis. The inhibition of survivin expression increased caspase-3 activity in T24 cells, which led to apoptosis. As such, in some modes of practice the high pressure injection method uses siRNA to target survivin for the treatment of bladder cancer.

As another example, anti-apoptotic proteins of the Bcl-2 family, such as bcl-2 and bcl-xL can be targets of gene therapy for the treatment of bladder cancer. To illustrate this type of technology, in one study the cytotoxic effects of bcl-2 and bcl-xL antisense-oligodeoxy-nucleotides (AS-ODNs) in benign urothelial and transitional cell carcinoma (TCC) cell lines were investigated (Gabriel, U. (2008) Oncol Rep. 20:1419-23). Bcl-2 AS-ODNs showed higher cell mortality in TCC cells, whereas toxic effects on normal urothelium was minor.

The invention also contemplates delivery of a composition containing a nucleic acid that results in increased expression of cytokines useful for the treatment of pelvic diseases. For example, the nucleic acid can encode interleukin-15 (IL-15), which can stimulate the CD8(+) T-cell and natural killer (NK) cell proliferation. To illustrate this type of technology, in one study intravesical liposomal IL-15 gene delivery and its antitumor effect were tested in a mouse orthotopic bladder cancer model. (Matsumoto, K., et al. (2011) Hum Gene Ther. 22:1423-32), using transurethral delivery of liposome-mediated plasmids. Instillation with IL-15 gene plasmid showed inflammatory cells induced around the tumors, and infiltration of CD8(+) T cells around the tumor nest. After the intravesical IL-15 gene therapy, the growth of rechallenged subcutaneous MBT-2 cells in surviving mice was inhibited again via tumor-specific cytotoxic T lymphocytes.

Another cytokine useful for gene therapy for the treatment of bladder tumors is IL-23, in the sense that it can provide a tumor vaccine effect and can be used to combat tumorogenic growth. IL-23 plays a role in the inflammatory response against infection, and upregulates matrix metalloprotease MMP9 expression, increases angiogenesis, and reduces CD8+ T-cell infiltration, and has been implicated in the development of cancerous tumors. To illustrate this type of technology, in one study an expression vector containing the IL-23 gene was introduced into mouse bladder carcinoma (MBT2) cells, and mice vaccinated with the MBT2/IL-23 cells inhibited the tumour growth of parental MBT2 cells injected at a distant site (Kuramoto, T., et al. (2010) BJU Int. 108:914-21). CD8+ T cells were the main effector cells for the direct antitumour effect.

Another useful gene for providing protective anti-tumor immunity is the CD40 ligand (CD40L). CD40L is a member of the TNF superfamily and primarily expressed on activated T cells. CD40L-CD40 interaction can induce activation in an antigen-presenting cell (APC) in association with T cell receptor stimulation by MHC molecules on the APC. To illustrate this type of technology, in the orthotopic mouse model of bladder cancer, following intravesical instillation a SA-sCD40L fusion protein was durably immobilized on the biotinylated mucosal surface of bladder wall (Zhang, Z., et al. (2011) Acta Oncol. 50:1111-8). SA-sCD40L treatment prolonged the survival of MB49 tumor-bearing mice and cured 50% of mice with MB49 superficial bladder. In another study, patients with invasive bladder cancer scheduled for cystectomy or patients with T(a) tumors were treated with three cycles of intrabladder Clorpactin™ WCS-90 (sodium oxychlorosene) prewash, followed by AdCD40L, which is an adenoviral vector expressing the CD40 ligand (AdCD40L) (Malmström, P. U., et al. (2010) Clin Cancer Res. 16:3279-87). Patients experienced no adverse events to the vector therapy, and gene transfer was detected in biopsies, and bladders were heavily infiltrated with T cells. Histologic evaluation indicated that AdCD40L therapy reduced the load of malignant cells.

The invention also contemplates delivering agents via the high pressure delivery system that provide control over gene products that cause transcriptional silencing by CpG island methylation of tumor suppressor genes, and which can be used to treat cancerous growths. For example, depletion of the DNA methyltransferase DNMT1 in human bladder cancer cells has been shown to induce demethylation and reactivation of the silenced tumor-suppressor gene CDKN2A. To illustrate this type of technology, and in one study, selective depletion of DNMT1 using either antisense or siRNA resulted in lower cellular maintenance methyltransferase activity, global and gene-specific demethylation and re-expression of tumor-suppressor genes in human cancer cells (Robert, M. F., et al. (2003) Nat Genet. 33:61-5). Specific depletion of DNMT1 potentiated the ability of 5-aza-2'-deoxycytidine to reactivate silenced tumor-suppressor genes.

In some modes of practice, in addition to the high pressure delivery of the large molecular therapeutic according to methods of the invention, treatment can optionally include the administration of one or more chemotherapeutic agents. If desired, one or more chemotherapeutic agents can be administered using any suitable route. In some cases, the chemotherapeutic agents can be administered intravesically, which can be done using a standard catheter, or using the high pressure injection device as described herein. Chemotherapeutic agents that have been used to treat bladder cancers include N,N'N'-triethylenethiophosphoramide (ThioTEPA), adriamycin (doxorubicin, ADM), epirubicin (EPI), mitomycin C (MMC), valrubicin (AD32), pirarubicin (THP), gemcitabine, apaziquone (EOquin™), and Vicinium™ (anti-Ep-CAM humanized scFv-exotoxin A fusion protein).

The invention also contemplates treating interstitial cystitis/painful bladder syndrome (IC/PBS) with a large molecule therapeutic agent via the high pressure delivery device. IC/PBS is a condition that manifests itself in discomfort or pain in the bladder and surrounding pelvic region. The cause of IC/PBS is unclear, but symptoms resemble those of bacterial infection, without infection being present. To illustrate this type of technology, one type of gene therapy to treat IC/PBS has involved the targeted and localized expression of enkephalin in afferent nerves that innervate the bladder by gene transfer using replication-defective herpes simplex virus (HSV) vectors in a rat model of bladder hyperactivity and pain (Yokoyama, H., et al. (2009) Hum Gene Ther. 20:63-71). Replication-deficient HSV vectors encoding preproenkephalin, which is a precursor for Met- and Leu-enkephalin were injected into the bladder wall of female rats. Functionally, enkephalin vector-treated animals showed reductions in bladder hyperactivity and nociceptive behavior induced by intravesical application of capsaicin.

Gene therapy for the treatment of a bladder disease can also be performed by placing a gene of interest under the control of a promoter that provides tissue-specific expression in bladder tissue. The uroplakins (UP) are structural proteins and fundamental components of urinary tract epithelium. Two uroplakins genes (UP1a and UP2) are transcribed only in urothelium, and are therefore bladder-specific promoters. Gene therapy viral vectors under the control of a UP promoter could be used to drive therapeutic gene expression in high-UP-expressing transitional cell carcinoma. (Olsburgh, J., et al. (2003) *J. Pathol.* 99:41-49) A uroplakin II promoter was used in the construction of CG8840, a urothelium-specific adenovirus variant that eliminated established bladder tumors in combination with docetaxel (Zhang, J., et al. (2002) *Cancer Res.* 62:3743-50).

Another target of gene therapy can be genes that modulate the assembly of the cell's cytoskeleton. For example, gelsolin is regulator of actin filament assembly and disassembly. Gelsolin is an actin regulatory protein that is undetectable or reduced in human bladder tumors compared with normal epithelial cells. To illustrate this type of technology, in one study recombinant adenovirus encoding wild-type gelsolin (Ad-GSN) was transduced into human bladder cancer cell lines KU-7 and UMUC-2 (Sazawa, A., et al. (2002) J Urol. Sep;168:1182-7). KU-7 cells were introduced into the bladder of nude mice, followed by 3 injections into the urethra with Ad-GSN. Bladder cancer cell growth was inhibited after these cells were transduced with Ad-GSN in vitro.

Another pelvic disease that can be treated using the high pressure injection system of the current invention is kidney disease. For example, proteinuria (albuminuria) is a condition in which urine contains an abnormal amount of protein, which is thought to result from damaged glomeruli of the kidney. As another example, diabetic nephropathy is a progressive disease where the capillaries in the kidney glomeruli undergo angiopathy, and caused by diabetes mellitus. As another example, polycystic kidney disease (PKD) is a cystic genetic disorder of the kidneys. MiRNA expression has been shown to differ between the kidney and other organs as well as between different kidney regions, and have been found to be functionally important in models of PKD and diabetic nephropathy. The deletion of an endoribonuclease in the RNase III family called Dicer, which cleaves dsRNA and pre-miRNA into short siRNA, results in proteinuria and severe renal impairment in mice. In some modes of practice, modifying the expression of Dicer and/or miRNAs involved in the kidney disease by injection of the therapeutic composition using the high pressure injection device is another contemplated method of treatment (Li, J. Y., (2010) Nephrology, 15:599-608).

Chronic kidney disease (CKD) is also characterized by accumulation of extracellular matrix. Myofibroblasts that are α-SMA-positive which produce large amounts of TGF-β1 are thought to play an important role in the development of interstitial fibrosis. To illustrate this type of technology, in one study inhibition of fibrosis by hepatocyte growth factor (HGF) was examined using HGF transgenic mice (HGF-Tg) with angiotensin II (Ang II) infusion (Iekushi, K., et al. (2010) J Hypertens. 28:2454-61). HGF-Tg mice showed significantly decreased Ang II-induced renal fibrosis and lesser numbers of interstitial myofibroblasts. The antifibrotic action in HGF-Tg mice was concordant with a decrease in TGF-β1, collagen type I and IV mRNA expression and an increase in MMP-2 and MMP-9 expression. Furthermore, HGF-Tg mice treated with Ang II showed apoptosis of myofibroblasts. Inhibition of the FAK-ERK-MMP signaling cascade by specific inhibitor or siRNA significantly decreased HGF-induced myofibroblast apoptosis. One miRNA (miR-192) can also act as an effector of transforming growth factor-β activity in the high-glucose environment of diabetic nephropathy (Li, J. Y., (2010) Nephrology, 15:599-608).

In another study, thrombospondin-2 (TSP-2) was investigated an endogenous regulator of matrix remodelling and inflammation in an anti-Thy1 glomerulonephritis model of experimental kidney disease (Daniel C, et al. (2009) Am J Physiol Renal Physiol. 297:F1299-309). TSP-2 overexpression inhibited both glomerular endothelial and mesangial cell proliferation, resulting in a reduced glomerular cell number and glomerular tuft area.

Autoimmune glomerulonephritis is associated with a significant immune response with glomerular crescentic formation and fibrosis in the kidney. Overexpression of Smad7, which is a member of the SMAD family of proteins, transduces extracellular signals from transforming growth factor beta ligands to the nucleus where they activate downstream TGF-β gene transcription and attenuates both renal fibrosis and inflammation in rat remnant kidney. In another study, the Smad7 gene was transfected into the kidney and its overexpression blocked both renal fibrosis and inflammatory pathways (Ka, S. M., et al. (2007) J Am Soc Nephrol. 18:1777-88).

Therefore, in another mode of practice, the therapeutic composition delivered by the high pressure injection device provides a therapeutic agent which increases HGF expression, decreases TGF-β1 expression, or interferes with the FAK-ERK-MMP signaling cascade.

A nucleic acid-containing therapeutic compositions for treatment of kidney diseases can be included in a nonviral, viral, or a cellular vector. For kidney tissue, one efficient vector for in vivo transfection has shown to be adenovirus. For example, glomeruli, blood vessels, interstitial cells, and pyelum can be transfected with high efficiency using an adenovirus that carries a nucleic acid of interest.

Recombinant human EPO (hEPO) has been successfully used to treat anemia associated with kidney disease using carried out for a considerable period of time. A genetic therapy approach for the production of hEPO is desirable because of the disadvantages of administration of the hEPO protein. To illustrate this type of technology, in one study an adenovector expressing EPO was constructed by inserting the human EPO cDNA was inserted into the pAd-lox shuttle vector containing the cytomegalovirus (CMV) promoter and simian virus-40 (SV40) polyA site (Lippin, Y., et al. (2005) Blood, 106:2280-2286). The adenovector was used to create autologous genetically modified tissue that expressed hEPO.

In other modes of practice, the method of the invention is used for the treatment of a prostate disease. For example, the treatment of prostate cancer can be performed by delivering a composition having a nucleic acid which alters the expression of an immunomodulatory gene, and apoptosis gene, a tumor suppressor gene, or an anti-oncogene in prostate tissue.

For example, gene therapy using the prostate-specific antigen (PSA) sequence can be used for treatment. PSA is a well known marker for prostate cancer the diagnosis and management. To illustrate this type of technology, in one study an enhancer/promoter construct 5' end of the human PSA gene was inserted into adenovirus type 5 DNA to create a prostate-specific enhancer-containing virus (Rodriguez, R., et al. (1997) Cancer Res. 57:2559-63). The virus destroyed large androgen-sensitive human prostate adenocarcinoma (LNCaP) tumors and abolished PSA production in nu/nu mouse xenograft models with a single intratumoral injection.

In another study, a functional DNA-lipid complex encoding the interleukin 2 (IL-2) gene was administered to patients with locally advanced prostate cancer (CaP) (Belldegrun, A., et al. (2001) Hum Gene Ther. 12:883-92). The IL-2 gene therapy was well tolerated, and there was evidence of systemic immune activation, based on an increase in the intensity of T cell infiltration seen on immunohistochemical analysis of tissue samples from the injected tumor sites, and increased proliferation rates of peripheral blood lymphocytes that were cocultured with patient serum collected after treatment. A transient decreases in serum prostate-specific antigen (PSA) was seen in most patients.

The system and methods of the invention are used to treat a disease or condition of present in at a location in the female genitourinary tract. In some modes of practice, the high pressure injection is used to treat a fibroid, such as a uterine fibroid, or a cancerous growth in endometrial lining. Uterine fibroids are benign tumors that originate from the uterine myometrium (smooth muscle) and the accompanying connective tissue of the uterus. Fibroids include uterine leiomyomas, fibromyomas, and fibromas. For instance, a therapeutic composition having can be injected into fibroids, or the uterine artery.

To illustrate this type of technology, in one study Eker rats with MRI-confirmed uterine leiomyomas were provided with direct intra-tumor injection of adenovirus (Ad)-mediated delivery of herpes simplex virus 1 thymidine kinase gene (HSV1TK) followed by ganciclovir (GCV) treatment (Hassan, M., et al. (2009) Gynecol Obstet Invest. 68:19-32). The adenovirus treatment decreased uterine fibroid volume, increased caspase-3 activity, Bax expression, and TUNEL apoptosis marker, and it decreased cyclin D1, PCNA, Bcl2, and PARP protein expressions.

The system and methods of the invention can also be used to treat a disease or condition of present in at a location in the lower gastrointestinal tract, such as the rectum or large intestine.

The therapeutic composition delivered via the high pressure delivery device can have a therapeutic agent (e.g., nucleic acid or protein) in an amount sufficient to provide a therapeutic effect in a patient. The amount of the therapeutic agent provided to a patient can depend on various factors, such as the pharmacodynamics of the therapeutic agent, including the therapeutic agent potency, which is a measure of the quantity of therapeutic agent needed to produce a desired effect, the therapeutic agent half life or stability, the ability of the therapeutic agent to reach its site of action (e.g., the ability of a nucleic acid to enter an intracellular space), the amount of tissue to be treated, the duration of treatment, and the like. The amount of therapeutic agent provided to a patient can be described as a single dose, or as a cumulative dose over a determined time period.

For example, a nucleic acid can be provided to a patient in an amount over a wide dosage range, such as from nanograms to milligrams. In many modes of treatment, and amount of nucleic acid in the nanogram to microgram range is administered to the patient, such as from about 10 nanograms to about 900 micrograms, about 100 nanograms to about 100 micrograms, or about 500 nanograms to about 10 micrograms. A therapeutic polypeptide can be administered to a patient in the same dose ranges.

Composition which can be delivered by the high pressure jet injection devices can include one or more excipient components to enhance delivery of the nucleic acid into the cells, or to promote its integration and/or function in the cells. In some preparations the excipient material is a non-viral material that enhances nucleic acid delivery, by promoting uptake of the nucleic acid into the cell. Material having a positive charge such as cationic lipids or polycations like polylysines and polyethylenimines can condense nucleic acids into small particles. Examplary excipient materials include polyamidoamines, dendrimers, peptide carriers, lipopeptides, and lipopolymers. The charge density of a polycation (the carrier) can operate to complex and the then cause the release of the gene from the complex in the cytosol.

Specific examples include multivalent polycationic beta-cyclodextrins having a beta-cyclodextrin core oligoethyleneamine arms to facilitate DNA binding, encapsulation, and cellular uptake (Journal of the American Chemical Society (2008) 130:4618-4627); and polyethylene glycol (PEG)-polyethylenimine (PEI) conjugate polymers (U.S. Pat. No. 7,060,498).

The composition can optionally include small solid particulates. Small solid particulates can be in the form of microparticles, microspheres, nanoparticles, or nanospheres, can include a large molecule therapeutic agent, and can be used to facilitate delivery of the therapeutic agent into the pelvic tissue. The therapeutic agent present in the small solid particulates can be released to provide a therapeutic effect after the high pressure injection. If such particles or other particles are mixed with the liquid in the pressure chamber, these are also ejected during the delivery process and can behave in a manner similarly to the liquid surrounding them.

The use of microparticles, microspheres, nanoparticles, or nanospheres can be beneficial in to protect large molecule therapeutic agent from the sheer forces associated with the ejection of material from the high pressure delivery device. In these cases, therapeutic agent within the particulate, not directly on the particulate surface, is protected from these forces during delivery.

In some preparations, the small particulates include the therapeutic agent and an excipient agent used to form the particulates that is not readily soluble in water, so they can be maintained in a particulate state. In some preparations the small particulates include the therapeutic agent and a biodegradable polymer. Exemplary biodegradable polymers include polyesters such as polylactic acid, poly(lactide-co-glycolide), polycaprolactone, polyhydroxybutyrate, polyorthoesters, polyphosphazine, polymethylidenemalonate, polyalkeneanhydrides, polypeptides, polyanhydrides, and the like.

An exemplary jet injection device will now be discussed. The jet injection device ejects a therapeutic "fluid" from a distal end of an elongate shaft inserted into or placed adjacent to the patient tissue. The devices can include multiple orifices that may be stationary or moveable relative to a shaft of the device, for ejecting a pressurized fluid at multiple locations. Embodiments that include multiple orifices can include an extended, expanded, or extendable chain, string, array, or sequence (e.g., "daisy chain"). Orifices may be located at an extension mechanism ("orifice extension") such as extendable or fanning needles or needleless fluid delivery orifices.

The pressurized fluid source can include a source of fluid and a source of pressure. The pressure source may be mechanical (such as a spring), pneumatic, hydraulic, electric, etc., as will be understood. Further, the pressure source may be mechanically or electronically controlled. The pressure source can cause a fluid contained in a fixed or variable volume chamber to be pressurized to a transient pressure, at the injection orifice, that is sufficiently high to allow the fluid to be ejected from the injection orifice with sufficient force to penetrate internal tissue such as to traverse the urethra and to then penetrate a desired distance into target pelvic tissue. An endoscope or other optical feature can be included for use with the injection device.

Various device structures, components, methods and techniques described and depicted in U.S. Patent Publication No. 2006/0129125 and International Publication No. WO2007/079152 are envisioned for use, alone or in combination, with the present invention. As such, the entire disclosures of the above-referenced publications are incorporated herein by reference.

In one embodiment, such as that shown in FIG. 1, a jet injection catheter device or system 10 can include a proximal portion 12 and a distal portion 14, and a shaft or body portion 16 extending therebetween. The proximal portion 12 generally includes a handle 18, and a connection port or assembly adapted to interconnect with a fluid source 36. The fluid source 36 is in operative and fluid communication with the proximal portion 12 via a conduit 34. The fluid source 36 can include a reservoir and pressure source capable of pressurizing and advancing fluid contained in the source. The fluid source can be generally "remote" (FIG. 1) from the proximal portion or the distal portion 14, or provided generally proximate or directly attached to the device components.

A working lumen or channel 17 extends within the shaft 16 and contains a fluid delivery lumen 22 such that the lumen 22 is adapted to move longitudinally along the length of the body 16 to allow the distal end of the fluid delivery lumen 22 to extend from the tip of the distal portion 14 as an orifice extension. The high-pressure injectate is delivered to the target tissue from the fluid delivery lumen 22. In particular, the injectate traverses from the fluid source 36, into the working channel 17, and out of the fluid delivery lumen 22. Shaft 16 can include a fiber optic feature 30, e.g., an endoscope device, having a light source 20 to transmit light to the distal portion 14. In one embodiment, the fluid source 36 can include a fully-pneumatic source or injection console. Such a console configuration promotes safety and functionality. Power for the system 10 and console can come from a $CO_2$ tank in which pressure is monitor by a gauge.

A variety of materials may be used to form portions or components of the systems 10, including nitinol, polymers, elastomers, fluid systems and components, thermoplastic elastomers, metals, ceramics, circuitry, springs, wires, plastic tubing, and the like. The device 10, and its components and methods may have a number of suitable configurations known to one of ordinary skill in the art.

A method for the delivery of the therapeutic agent can involve inserting and then moving shaft or body portion 16 of the device through one or more parts of the urogenital tract of a male (urethra, bladder) or female (vagina, urethra, bladder, uterus, fallopian tubes), or the lower gastrointestinal tract (rectum, large intestine) to position the distal portion 14 end of the device at a desired treatment site. The device can then be actuated to eject the liquid composition at high pressure from the distal end of the device into the tissue. Liquid composition can be delivered in a single ejection of fluid, or more than one ejection of fluid. The distal end of the device can be moved slightly between injections to target a larger area of tissue.

A fluid stream or jet of composition ejected from an aperture of apertures at the distal end of the device can be of a size (e.g., diameter), velocity, pressure, and volume to penetrate into the tissue in a desired manner. The stream can be considered to be a relatively high velocity, high pressure, small diameter jet that enters and disperses within the tissue. The therapeutic composition can be carried as a multi-directional collection of particles (e.g., a "cloud") or droplets within the plaque. The injection pressure refers to the stagnation pressure of the impinging jet, which is an important factor that determines the penetration capability of the injected fluid. The pressure p at the aperture or outlet is equivalent to the average stagnation pressure across the outlet area. Stagnation pressure is the pressure exerted by moving fluid when forced to come to rest, for example, by impingement on a target.

Exemplary pressures of a fluid at a pressure chamber can be at least 100 pounds per square inch (psi) (~0.7 megapascal (MPa)), for example, such as in the range of about 140 psi (~1 MPa) to about 4000 psi (~27.5 MPa), and more specifically in the range of about 140 to about 2000 psi (~13.8 MPa) are contemplated for injecting the therapeutic composition into tissue of a target region of the pelvic area. Injection pressures for treatment of pelvic tissues may be lower that what is typically used for epidermal needless injections (E.g, see Shergold, O. A., and Fleck, N. A. (2004). Proc. R. Soc. Lond. A., 460:3037-3058).

It is believed that that impact of the fluid stream or jet on the target tissue creates of a hole in the tissue through a cracking process. The accumulation of injected liquid slows down until it reaches a maximum point as the hole becomes deeper. Stagnation of the jet at the end of the hole expands the liquid into the tissue in a spherical pattern (Schramm-Baxter J, Mitragotri S (2005). J. Control. Rel., 106(3): 361-373.).

The duration of injection of the fluid stream or jet of the therapeutic composition can be performed for a desired period of time. In some methods of injecting, the duration of injection is controlled by one or more feature(s) of the injection device, such as a solenoid or valve, in order to meter the flow or stream of the composition from one or more apertures at the distal end of the device. The injection can include one or more high pressure "pulses" of the composition from one or more apertures. The duration of a pulse can be short such as in the range of about 5 milliseconds to about 1 second, or more specifically in the range about 50 milliseconds to about 0.6 seconds.

Small quantities of liquid are delivered to target pelvic tissue using the high pressure injection device. Cubic millimeters of liquid can be ejected from the distal end of the device under high pressure to facilitate delivery of the therapeutic substance to pelvic tissue. In some modes of practice a quantity in the range of about 0.1 $cm^3$ to about 2 $cm^3$, or more specifically about 0.25 $cm^3$ to about 1 $cm^3$ can be delivered to pelvic tissue per pulse of the high pressure injection device. Treatment can include a series of short pulses to deliver a desired amount of composition to target tissue in the pelvic area.

In some modes of practice, the distal end of the device is moved between pulses to change the direction and/or location of the injected therapeutic composition. For example, in use the shaft or body portion of the device is moved internally in the body to position the distal end at different tissue locations between pulses. Movement can be carried out in a proximal to distal direction, rotationally, or both. The treatment area can be targeted and very small, wherein only a single pulse can provide the desired treatment, or the treatment area can be larger, wherein multiple pulses are performed after positioning the distal end of the device at different locations in the body.

What is claimed is:

1. A system for delivering a therapeutic agent to pelvic tissue comprising (a) a high pressure delivery device comprising a pressure source, a fluid compartment that can house a therapeutic composition, and a distal end configured for placement at a location in the male or female urogenital tract or lower gastrointestinal tract selected from bladder, prostate, urethral, kidney, vaginal, and endometrial tissues, wherein said device is capable of delivering the composition from a distal end of the device at a pressure in the range of 100 psi to 4000 psi, and (b) a therapeutic composition comprising a nucleic acid or a polypeptide for treating or preventing a disease of the pelvic tissue, wherein the nucleic acid or polypeptide is present in a nanoparticle or microparticle; said nanoparticle or microparticle comprising an excipient polymeric material selected from the group consisting of polylactic acid, poly(lactide-co-glycolide), polycaprolactone, polyhydroxybutyrate, polyorthoesters, polyphosphazine, polymethylidenemalonate, polyalkeneanhydrides, polypeptides, and polyanhydrides.

2. The system of claim 1 wherein the high pressure delivery device is configured to deliver the composition to the tissue using a pressure in the range of 140 psi to 2000 psi.

3. The system of claim 1, wherein the high pressure delivery device is configured to deliver the composition having a volume in the range of 0.1 cm$^3$ to 2 cm$^3$.

4. The system of claim 3 wherein the volume is in the range 0.25 cm$^3$ to about 1 cm$^3$.

5. The system of claim 1 wherein the high-pressure injection device comprises a distal portion comprising a shaft configured for insertion into the urethra of the subject.

6. The system of claim 1 wherein the high-pressure injection device comprises a needleless distal end having one or more aperture(s) for the ejection of the composition.

7. The system of claim 1 wherein the distal end is configured for placement at bladder tissue.

8. The system of claim 1, wherein the nucleic acid promotes apoptosis of the cells of the tissue the composition is injected into.

9. The system of claim 1, wherein the nucleic acid promotes an RNA interference pathway to modulate expression of a target gene.

10. The system of claim 1, wherein the nucleic acid is present in a nanoparticle.

11. The system of claim 1 wherein , Of preferred excipient polymers are selected from the group consisting of poly (lactide-co-glycolides), polyhydroxybutyrates, and polyorthoesters.

* * * * *